United States Patent [19]

White

[11] Patent Number: 4,549,529

[45] Date of Patent: Oct. 29, 1985

[54] MYOPIA ALLEVIATION PROSTHESIS

[76] Inventor: Thomas C. White, 1127 Holly Dr., Sioux Falls, S. Dak. 57105

[21] Appl. No.: 540,344

[22] Filed: Oct. 11, 1985

[51] Int. Cl.$^4$ .......................... A61B 19/00; A61F 1/00
[52] U.S. Cl. ................................ 128/1 R; 128/334 R; 128/DIG. 20; 128/DIG. 21; 623/4; 623/11
[58] Field of Search .......... 128/1 R, 334 R, DIG. 20, 128/DIG. 21, DIG. 25; 3/1, 13

[56] References Cited

U.S. PATENT DOCUMENTS

| | | | |
|---|---|---|---|
| 2,760,483 | 8/1956 | Tassicker | 128/1 R |
| 3,789,828 | 2/1974 | Schultz | 128/1 R |
| 3,817,237 | 6/1974 | Bolduc | 128/1 R |
| 3,831,583 | 8/1974 | Edmunds, Jr. et al. | 128/1 R |
| 3,883,902 | 5/1975 | Lynch | 3/1 X |
| 3,919,724 | 11/1975 | Sanders et al. | 3/1 X |
| 3,988,782 | 11/1976 | Dardik et al. | 3/1 |

FOREIGN PATENT DOCUMENTS 990219 1/1983 U.S.S.R. .................................. 3/13

OTHER PUBLICATIONS

"A Simplified Scleral Reinforcement Technique", by Frank B. Thompson, American Journal of Ophthalmology, vol. 86, No. 6, pp. 782-790, 1978.

Primary Examiner—Ronald L. Frinks
Attorney, Agent, or Firm—Gregory P. Kaihoi

[57] ABSTRACT

A prosthesis having an elongated strip of flexible material bearing intermediate its length a pressure pad, the strip ranging in length from about 50 to about 75 mm. The strip is passed behind the globe of the eye so that the pressure pad rests against the eye wall at a location obverse to the macula. The ends of the strip are attached, as by sutures, to the sclera, causing the pressure pad to press anteriorly upon the eye wall and to move the macula forwardly. Various pressure pads, including adjustable pads, such as pads that are inflatable, are disclosed.

24 Claims, 14 Drawing Figures

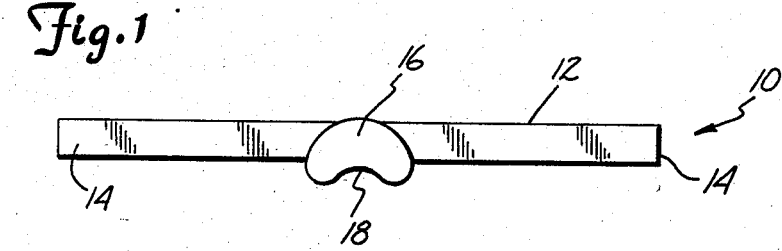
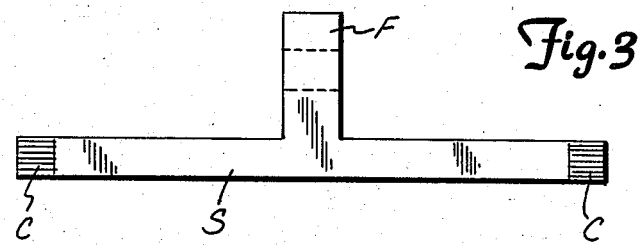
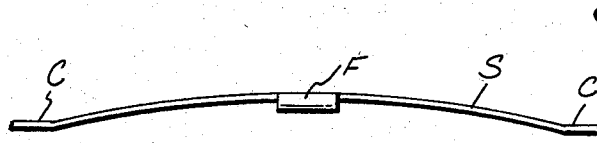
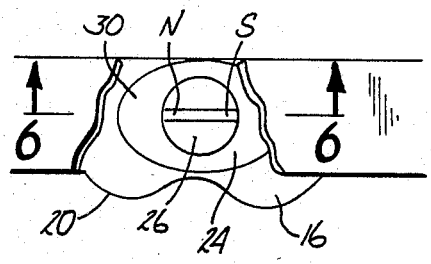

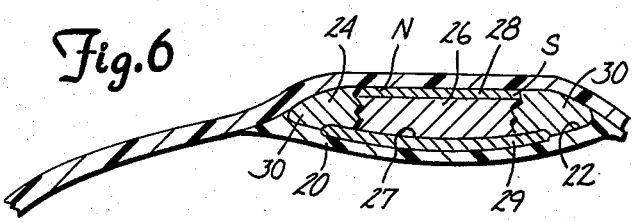
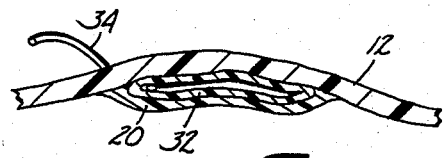
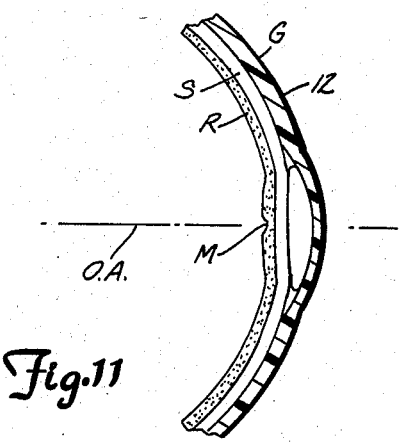
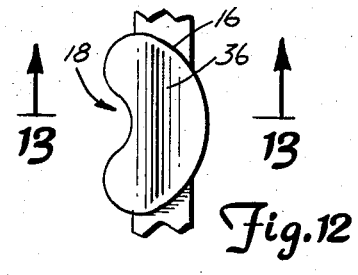
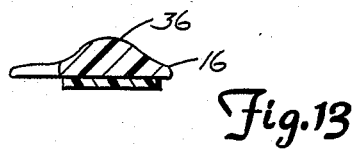
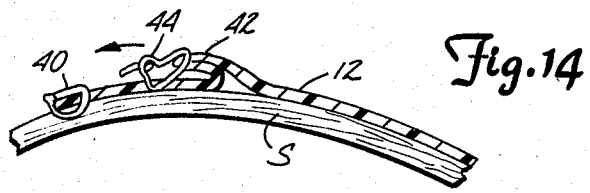

MYOPIA ALLEVIATION PROSTHESIS

FIELD OF THE INVENTION

The invention relates to the field of medicine and particularly to prostheses for improving the vision of myopic patients.

BACKGROUND OF THE INVENTION

A patient with normal vision is able to appropriately change the shape of the natural lens so as to focus an image upon the retina, and particularly upon the retinal macula. Myopic persons are unable to focus upon distant objects because the image thereof is formed a short distance (often measured in fractions of a millimeter) in front of the macula. There are various causes of myopia, among which may be listed the failure of the natural lens to change shape sufficiently, abnormal corneal curvature, and an abnormally long eye globe measured in the direction of the optical axis.

Eyeglasses commonly are employed to correct myopia of not greater than several diopters. Contact lenses can be used to correct myopia to the extent of perhaps twenty diopters. A surgical procedure known as a radial keratotomy has been employed in recent years to at least partially correct myopia, the procedure involving making radial, partial-thickness incisions in the cornea for the purpose of slightly flattening the cornea. Another surgical procedure, keratomilieusis, involves removal of a partial thickness corneal button, freezing and grinding the inner-side of the button to produce increased or decreased concavity, and then reattaching the corneal button, this procedure also tending to flatten the cornea. The surgical procedures thus described depend greatly upon the technical expertise and manual dexterity of the surgeon, and may in some cases lead to scarring of the cornea or to unintentional invasion of the anterior chamber with the consequent danger of infection. Further, a great deal of judgment must be used with respect to the depth, placement and number of radial incisions in the radial keratotomy procedure and in the degree of tissue removal in the keratomilieusis autograft procedure, and perfect results are seldom obtained. Trauma to the eye in the vicinity of the limbus, of course, may result in the onset of glaucoma.

The prostheses and surgical routines referred to above each have, as their object, a refractive correction anterior to the natural lens.

In the conditions known as progressive axial myopia and posterior staphyloma, the enlargement of the scleral and uveal coats of the eye results in stretching, thinning and deterioration of the retinal nerve tissue, which by its nature cannot grow. The interocular pressure in the globe itself tends to cause the globe to bulge out rearwardly. This, in turn, may cause structural changes in the retina leading to optically uncorrectible decreases in vision. In an effort to support the rearward portion of the globe against further distension and traction on the retina, scleral reinforcement techniques have been developed in which a band of scleral tissue is passed about the posterior portion of the globe to strengthen the globe. This procedure is particularly well reported in Frank B. Thompson, *A Simplified Scleral Reinforcement Technique*, AM. J. Opthalmol 86:782-790, 1978. In the reported procedure, a band of scleral tissue terminating in corneal portions and taken from a donor eye was passed posteriorly about the globe of an eye, the corneal end portions being sutured to the globe anteriorly of its equator. Although such slings by themselves may occasionally reduce an ectatic posterior staphyloma, the rearward portion of the globe is at best strengthened to prevent further distension and to limit the progression of posterior enlargement of the globe.

BRIEF DESCRIPTION OF THE INVENTION

The present invention provides a prostheses for myopic eyes and comprises an elongated strip of flexible, and desirably longitudinally elastic or substantially inextensible, material, the length of which may range from about 50 to about 75 mm. Intermediate its length, a pressure pad is provided along its inner surface, the pad being flexible but being desirably substantially incompressible through its thickness. In use, the prosthesis is passed posteriorly of the eye globe with the pressure pad in contact with the globe on the obverse side of the eye wall from the macula, and the ends of the strip are sutured to the sclera anteriorly of the equator of the globe. The pressure pad, pressing inwardly upon the posterior portion of the eye wall obverse to the macula, applies sufficient force anteriorly to the globe parallel to the optical axis of the eye so as to force the macula axially inwardly, e.g., the rearward wall of the globe is indented slightly toward the cornea of the eye, thereby shortening the distance between the macula and cornea to improve the formation of an image on the macula and reduce traction on retinal elements as may be desired. Since the macula need be moved axially inwardly of the globe toward the cornea only a very short distance, commonly measured in fractions of a millimeter for many cases of myopia, the thickness of the pressure pad, the tension in the strip, or both may be varied so that when the prosthesis is in place, the macula is correctly spaced from the cornea. In this manner, a variably controlled indentation of the posterior ocular segment can be accomplished to reduce the axial length of the globe, thereby correcting mild to severe myopia and, as may be desired, reducing traction on retainal elements to prevent structural damage resulting in permanent optically uncorrectable decreases in vision.

Accordingly, the invention, in one embodiment, involves positioning a prosthesis of the invention behind the globe with the pressure pad bearing anteriorly against the obverse side of the eye wall from the macula to force the latter anteriorly to improve the formation of an image on the macula.

Since the macula is spaced only a short distance (about 5 mm.) from the optic nerve, and since pressure against the optic nerve should be avoided, the pressure pad of the invention preferably has a recessed edge to accommodate free passage of the optic nerve.

If desired, the thickness of the pressure pad may be externally adjusted after positioning of the prosthesis so as to permit adjustment of the axial position of the macula. Hence, another embodiment of the invention involves a method of positioning behind the globe a prosthesis of the invention having a pressure pad, the thickness of which is externally adjustable, and thereafter adjusting the thickness of the pressure pad so as to appropriately axially position the macula so that images from distant objects are focused upon the macula. The prosthesis in one embodiment may include a pad comprising an inflatable reservoir, and inflation means, typically a thin tube, leading from the reservoir to permit external inflation thereof after surgical positioning of the prosthesis. The reservoir may be inflated with any appropriate fluid such as saline or, preferably, a hardenable polymeric substance. If a non-hardenable fluid such as saline or air is employed, then means must be provided for maintaining the fluid within the reservoir. If a hardenable, normally polymeric substance is employed, then, upon hardening of the substance, the inflation tube may be removed from the device.

In another embodiment, the pressure pad may include an internally threaded annular washer having therewithin an exteriorly threaded shaft, the shaft bearing magnetic means enabling exterior rotation thereof. The shaft may be provided with a bar magnet across its width, and rotation of the shaft within the washer may be affected by providing a strong magnet exterior and desirably, anterior to the eye and rotating the magnet about the optical axis of the eye.

DESCRIPTION OF THE DRAWING

FIG. 1 is a plan view of a prosthesis of the invention;
FIG. 2 is a side view of the prosthesis of FIG. 1;
FIG. 3 is a view, in plan, of a strip of corneoscleral tissue from a donor eye;
FIG. 4 is a side view of the tissue strip of FIG. 3, folded to provide a pressure pad intermediate its ends;
FIG. 5 is a broken-away, plan view of a modified device of the invention;
FIG. 6 is a cross-sectional view taken along line 6—6 in FIG. 5;
FIG. 7 is a cross-sectional view similar to that of FIG. 6 but showing another embodiment of the invention;
FIG. 11 is a broken-away, cross-sectional view of the rear wall of an eye showing a prosthesis of the invention in place;
FIG. 12 is a broken-away, plan view of a modificiation of the invention;
FIG. 13 is a cross-sectional view taken along line 13—13 of FIG. 12;
and
FIG. 14 is a broken-away, cross-sectional view showing a suturing method.

DESCRIPTION OF THE PREFERRED EMBODIMENT

Figure 8:
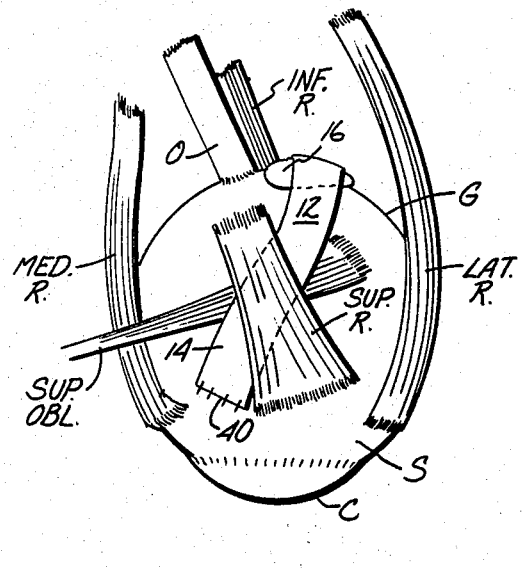
FIG. 8 is a largely diagramatic, broken-away top view of an eye to which the prosthesis of the invention has been secured.
Figure 9:
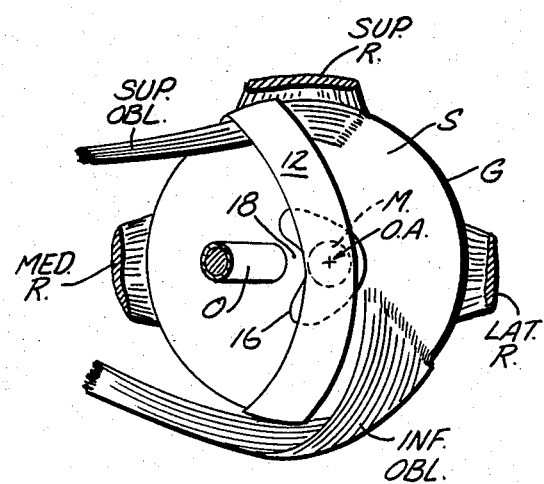
FIG. 9 is a rear view of the eye shown in FIG. 8.

Referring first to FIGS. 3 and 8–11, proper understanding of the invention can be aided by first identifying the relevant eye structure. The globe of an eye is shown generally as "G" and includes, anteriorly, a cornea "C". Movement of the eye is governed by the operation of six eye muscles of which the medial and lateral rectus muscles are designated "Med. R." and "Lat. R.". The superior and inferior rectus muscles are designated "Sup. R." and "Inf. R.". The superior and inferior oblique muscles are designated "Sup. Obl." and "Inf. Obl.". The optic nerve is designated "O", and, as is shown in FIG. 9, inserts into the globe medially of the optic axis "O.A.". With reference to FIG. 11, which is simplified for purposes of this disclosure, the sclera at the posterior portion of the eye wall is designated "S" and the retina, including its uveal layer, as "R". The macula, which is centered on the optical axis, is shown as "M", and is shown in phantom lines also in FIG. 9.

Referring now to the embodiment of FIGS. 1 and 2, the device of the invention is shown generally as (1) and comprises an elongated strip (12) having a length in the range of from about 50 to about 75 mm. The strip may be of any physiologically acceptable material such as donor scleral tissue or other tissue, woven polyester, silicone or siliconized fabric, and silk. The strip is flexible so as to closely conform to the outer surface of the globe of an eye. In one embodiment, the strip is inextensible; in another embodiment, the strip may be longitudinally elastically extensible. Particularly the end portions (14) of the strip are desirably suturable; that is, they are strong and tear or split-resistant so as to accept and retain sutures when the device is implanted in an eye. The strip (12) desirably is not greater than about 1.0 mm. in thickness, and the longitudinal edges of the strip (12) desirably are gently rounded or are soft or nonabrasive so as to avoid unintentional irritation or damage to the eye.

A pressure pad is designated (16) and is sewn, cemented or otherwise affixed to the strip (12) intermediate the length of the strip. The pressure pad may be of any useful size and shape, edges of the pad desirably are gently rounded and soft or otherwise nonabrasive. In one embodiment, the pad (16) may be substantially incompressible in its thickness direction, although the pad may be otherwise as flexible as desired.

The term "substantially incompressible" means that the pad, when urged anteriorly against the rearward eye wall segment, will preferentially indent the eye wall rather than mainly absorb anterior pressure through compression. Some compressability, of course, may be permitted. Since, when the device (10) is surgically positioned, the pad (16) comes into fairly close proximity with the optic nerve, the pad may be recessed along one edge as shown at (18) in FIG. 1 to accommodate passage of the nerve. The pad may be so affixed to the strip as to permit adjustment of the pad along the strip to a desired position. For example, the strip may pass slideably through loops or a channel carried by the pad. Preferably, however, the pad is nonmoveably attached to the strip.

As described more fully below, the surgical positioning procedure involves passing the strip (12) posteriorly about the globe of an eye and then fastening, as by sutures, the ends (14) of the strip to the sclera anteriorly of the equator of the eye and adjacent but spaced from the limbus. In this manner, the pad (16) is positioned directly behind the macula, and the forward axial pressure that is placed on the pad when the ends (14) of the strip are sutured tautly to the sclera causes the pad to push axially inwardly upon the eye wall, resulting in a slight but measurable anterior displacement, i.e., indentation, of the macula along the optical axis. The degree to which the macula may be displaced anteriorly will depend upon the tautness of the strip (12) and the thickness of the pad (16); since the tautness of the strip is limited by practical considerations involving the strength of the sutures and sutured scleral tissue, the anterior axial displacement of the macula depends largely upon the thickness of the pad (16).

In the embodiment thus described, different degrees of desired visual correction will be afforded through the use of pads having different, predetermined thicknesses and the amount of anterior pressure imparted to the pads. As shown in FIG. 11, when the device of the invention is properly positioned, the pad causes axial deformation or indentation of the posterior portion of the eye wall obverse to the macula, and also may deform the strip (12) at the site of the pad (16). The correlation between pad thickness and optical correction due to anterior displacement of the macula assumes that the tension in the strip (12) and its deformation due to the presence of the pad (16) can be largely controlled. The axial displacement of the macula from the cornea may be determined with precision (within about 0.1 mm.) by known ultrasound techniques at the time of surgery.

The ease of indenting the globe wall may be improved by utilizing an anterior chamber tap to release aqueous humor and thus control intraocular pressure as sutures holding the strip are drawn taut during surgery. If intraocular pressure is initially reduced, then, since the intraocular pressure will ordinarily be restored by the eye, it may be desirable to displace the macula axially forwardly a distance slightly greater than needed to correct vision since the macula will be displaced rearwardly slightly as intraocular pressure is rebuilt.

As mentioned above, the compressibility of the pad (16) in its thickness direction desirably is relatively slight and substantially less than the compressibility or deformability of the eye wall at its posterior surface obverse to the macula. That is, variations in pad thickness desirably are directly reflected in changes in the anterior displacement of the macula.

FIGS. 3 and 4 show the use of a strip (12) that is cut from a donor eye. Scleral tissue commonly is a somewhat fibrous tissue with the fibrous orientation running from the anterior to the posterior regions of the eye; hence, sutures that are placed in scleral tissue and that are subject to forces parallel to the fibrous orientation may cause the sclera to split or yield parallel to its fibers. Also, the strip (12) should be sufficiently long, as discussed above, as to extend from the pad (16) anteriorly about the globe of the eye for fixation to the sclera of the host eye at a point anterior to the equator of the eye and adjacent but spaced from the limbus. For these reasons, a strip of corneo-scleral material may be cut from a donor eye as shown in FIG. 3, the ends of the strip including portions of corneal tissue. The corneal tissue is comparatively strong and tear resistant, and can be readily sutured to the sclera of the host eye. The strip of eye tissue commonly will be approximately 50–75 mm. in length and desirably about 8 mm. in width, and will have a thickness in the range of about 0.5–1.0 mm. A pad (16), either made of artificial, desirably fibrous material such as polyester or of natural donor eye tissue (as by reflecting or folding a posterior flap "F" of scleral tissue back upon itself along the dashed lines as shown in FIG. 3) may be appropriately fashioned.

With reference to the embodiment shown in FIGS. 5 and 6, a web or membrane of soft, flexible material (20) such as silicone rubber may be fastened to the strip (12) to form a generally hollow cavity (22) within which may be supported an internally threaded, annular washer (24) of rigid plastic or metal or other rigid substance. A short, exteriorly threaded bolt (26) may be threadingly received in the washer, as depicted, the bolt desirably having a gently rounded surface (27) in contact with the membrane (20) or with a dished plate (29) itself in contact with the membrane (20). In this manner, as the bolt (26) is screwed inwardly or outwardly of the washer (24), the pressure of the bolt face (27) against the membrane (20) or plate (29), and hence the pressure of the membrane against the posterior portion of the eye obverse to the macula, may be adjusted. Magnetic means may be provided to permit adjustment of the position of the bolt, such means being depicted in FIGS. 5 and 6 as a small bar magnet (28) embedded in the outer surface of the bolt (26) and having north and south poles on either side of the axis of rotation of the bolt. In this manner, once the prosthesis has been affixed to the globe, the bolt (26) may be turned through appropriate manipulation of a large magnet about the head of the recipient so that the membrane displaces the macula forwardly along the optical axis the desired distance. This feature permits the thickness of the pad to be adjusted after affixation of the prosthesis so that the most appropriate axial length of the globe is obtained. Desirably, the threads of the washer (24) or bolt (26) or both, and the other surfaces that slide past one another are appropriately lubricated to enable the bolt to be easily turned within the washer. The edges (30) of the washer may be tapered as desired to reduce sharp exterior angles.

As described more fully below with reference to FIGS. 5 and 6, the anterior surface of the membrane (20) or plate (29) may be contoured to provide an astigmatic correction. In the embodiment of FIGS. 5 and 6 in which the bolt (26) may rotate but the membrane (20) and plate (29) do not, the orientation of an astigmatic corrective contour does not change as the bolt is rotated. If desired, of course, the plate (29) may be fixed to and rotatable with the bolt so that the orientation of the astigmatic correction may be adjusted as well. It will also be understood that the bolt (26) may be affixed to the plate (29), the membrane (20) or the strip (12) to restrain it from rotation, and the threaded washer instead may be provided with magnetic poles, the axial position of the bolt (26) thus being adjusted through rotation of the washer through magnetic coupling to an external magnet.

FIG. 7 shows another embodiment of the invention in which the interior of the pad is provided with an inflatable reservoir (32). Means for inflating the reservoir, typified as a small diameter tube (34), extends between the reservoir and the exterior of the device. When the prosthesis has been suitably affixed to the globe, the reservoir may be inflated with saline or other fluid through the tube (34) through the use of a hypodermic syringe or the like, the degree of inflation depending upon the desired anterior displacement of the macula. Desirably, a settable or hardenable fluid is used as the injection medium, one such fluid being a curable silicone rubber. In the latter embodiment, once the prosthesis has been affixed and the intraocular pressure has stabilized, the settable or hardenable fluid may be injected through the tube (34) into the reservoir (32) until the macula has been moved anteriorly the desired distance, following which that degree of inflation is maintained until the fluid solidifies. Exterior portions of the tube (34) can then be removed.

As mentioned above with reference to FIGS. 12 and 13, the surface of the pad (16) that comes into contact with the globe may be contoured to provide some astigmatic correction. As depicted in the drawing, the pad may be raised slightly in a direction normal to the optic axis to form an elongated bulge or rounded rib (36), the contour of which is transmitted to and is reflected to some extent by a similar curvature or contour of the macula. Although only a single contour change is shown in the embodiment of FIGS. 12 and 13, the pad may be contoured as desired.

Figure 10:
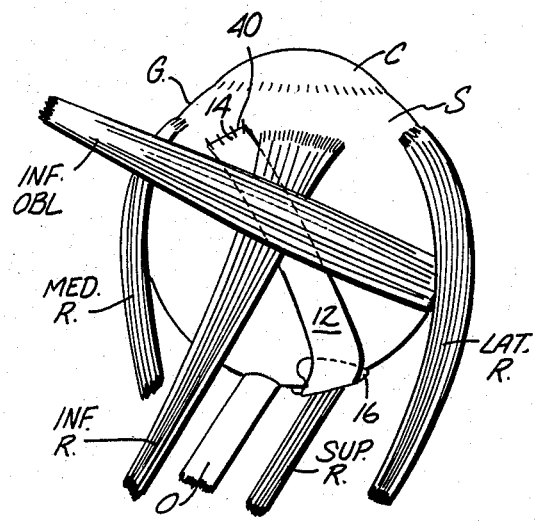
FIG. 10 is a bottom view of the eye of FIG. 8.

FIGS. 8–10 show a preferred positioning of the prosthesis of the invention when implanted in the eye, Tenon's capsule being omitted for purposes of clarity. The device of the invention commonly may be affixed without requiring any of the eye muscles to be severed. One end of the device is passed behind the globe and over the rearward globe surface obverse to the macula and laterally of the optic nerve "O". One end of the strip (12) passes superiorly over the superior oblique muscle and under the rectus muscle and is attached at its end (14) by means of sutures (40) or the like to the sclera of the host eye. The other end (14) of the prosthesis passes inferiorly under both the inferior rectus and inferior oblique muscles, and similarly is attached to the sclera of the eye by sutures (40) or the like. To permit the tension of the strip (12) to be adjusted postoperatively (as on an out-patient basis), the strip (12) may be doubled back upon itself as shown in FIG. 14 to provide an adjustable pleat, the doubled-back portion (42) being attached to the anterior portion of the strip by means of adjustable sutures (44) that can be drawn as taut as desired to provide optimum visual correction. Other tension-adjusting means, of course, may also be used.

When in place, the pad (16) is positioned directly against the eye wall obverse to the macula and is spaced laterally a short distance from the optic nerve. The recess (18) desirably formed in the pad tends to further reduce the possibility of contact between the pad and optic nerve. The strip (12) is held in place by the sutures (40) and by action of the eye muscles, particularly the superior and inferior rectus muscles and the superior and inferior oblique muscles, and the orientation of the strip against the eyeball generally follows a circumference of the eyeball passing through the point on the globe obverse to the macula. Further sutures can be added, as needed, to reduce any propensity of the strip to move once it has been correctly positioned.

Thus, the present invention provides a prothesis which can be readily used to improve the vision of nearsighted or myopic patients by displacing the macula of the retina anteriorly along the optic axis. The degree of macula displacement, resulting from indentation of the globe obverse to the macula, may depend, in one embodiment, upon the thickness of the pressure pad that is employed or upon strip tension, and in other embodiments upon the exterior adjustment of the pressure pad thickness after the prosthesis has been implanted. The prosthesis may be used as a plumbage in aid of further surgical procedures, as in the repair of retinal holes in the posterior polar region, the latter sometimes occurring in severe diabetic and trauma cases, and may also be used to reduce posterior staphyloma (or bulging of the globe in the region of the macula) to improve the vascular supply to the posterior retinal area and to reduce mechanical damage to the retina in the macular area.

While a preferred embodiment of the present invention has been described, it should be understood that various changes, adaptations and modifications may be made therein without departing from the spirit of the invention and the scope of the appended claims.

What is claimed is:

1. A prosthesis for improving the vision of myopic patients comprising
    an elongated strip of biologically acceptable material having suturable ends and which has a length ranging from about 50 to about 75 mm.; and
    a pressure pad carried by the strip intermediate its length for bearing against the eye wall obverse to the macula with sufficient axially applied force as to displace the macula axially toward the cornea of an eye to improve the formation of an image on the macula.

2. The prosthesis of claim 1 in which the pressure pad is provided with a recess along an edge thereof to accommodate passage of the optic nerve.

3. The prosthesis of claim 1 including exteriorly operable means for varying the thickness of the pressure pad when the prosthesis has been affixed to the eye.

4. The prosthesis of claim 3 in which said exteriorly operable means includes an internally threaded, annular washer carried by the pad and an exteriorly threaded bolt threadingly received in the washer for movement, upon rotation thereof, in a direction normal to the length of the strip, and magnetic means carried by the bolt enabling the latter to be rotated through manipulation of a magnetic field exterior of the eye of a patient.

5. The prosthesis of claim 4 wherein said pressure pad includes a nonrotatable, anterior facing membrane to receive axial pressure from said bolt and transmit such pressure to the eye wall.

6. The prosthesis of claim 3 wherein said externally operable means comprises an inflatable reservoir carried by the pad, and means enabling inflation of the reservoir externally of the eye.

7. The prosthesis of claim 1 wherein said pad has a surface contactable with the globe of an eye obverse to the macula, said surface having a predetermined asymmetric contour to provide astigmatic correction.

8. The prosthesis of claim 1 wherein the strip is longitudinally substantially inelastic.

9. The prosthesis of claim 1 wherein the strip is longitudinally elastic.

10. The prosthesis of claim 1 wherein the pad is substantially incompressible in its thickness direction.

11. A prosthesis for improving the vision of myopic patients comprising an elongated strip of biologically acceptable material which has a length ranging from about 50 to about 75 mm., and a pressure pad carried by the strip intermediate its length for bearing against the eye wall obverse the macula so as to indent the globe of the eye and displace the macula axially toward the cornea of an eye to improve the formation of an image on the macula, the pressure pad having a recess therein along an edge thereof to accommodate passage of the optic nerve, and the ends of the strip being of a suturable, rip-resistant material.

12. The prosthesis of claim 11 in which the intermediate portion of the strip and the pad are resiliently curved so as to fit snugly against the posterior wall of the globe of an eye obverse to the macula.

13. A method for improving the vision of myopic patients which comprises the steps of providing a prosthesis comprising a longitudinal strip of biologically acceptable material bearing intermediate its length a pressure pad, and affixing said prosthesis to the eye with the pressure pad bearing against the eye wall and causing anterior displacement of the macula along the optical axis of the eye to reduce the extent of myopia.

14. The method of claim 13 including the step of reducing intraocular pressure of an eye prior to affixation of the prosthesis by an anterior chamber tap, thereby rendering the posterior wall of the eye more susceptible to anterior displacement through application of the pressure pad thereagainst.

15. The method of claim 14 in which said pressure pad is of sufficient thickness as to displace the macula anteriorly a distance greater than that desired to improve vision, to thereby compensate for subsequent posterior movement of the macula in response to restoration of intraocular pressure.

16. The method of claim 13 including the step of providing an anterior chamber tap through which aqueous humor may escape as the macula is displaced anteriorly to thereby accommodate any intraocular pressure increase due to anterior, macular displacement.

17. A method of reducing the degree of myopia of a patient's eye which comprises
   (a) affixing onto the globe of the eye a prosthesis having a pressure pad positioned against the eye wall obverse to the macula, the prosthesis including means for externally varying the thickness of the pressure pad after such affixation; and
   (b) varying the thickness of the pressure pad to adjust the anterior displacement of the macula of the eye along its axis to improve image formation upon the macula.

18. The method of claim 17 wherein said pressure pad includes an annular, internally threaded washer and an exteriorly threaded bolt received threadingly within the washer, the bolt including magnetic means providing north and south poles diametrically opposed across the axis of rotation of the bolt, the method including the step of applying a magnetic field adjacent the eye upon which the prosthesis is affixed, and varying the rotational position of said magnetic field to cause rotation of the bolt within the washer, thereby varying the thickness of the pressure pad.

19. The method of claim 17 wherein the pressure pad includes an inflatable reservoir and wherein the prosthesis includes exteriorly operable means for inflating the reservoir after affixation of the prosthesis to the globe of an eye, the method including the step of inflating the reservoir to adjust the anterior displacement of the macula to a position nearer the position of image formation within the eye.

20. The method of claim 19 wherein the reservoir is inflated with a solidifiable fluid, the method including the step of maintaining the desired inflation of the reservoir until said fluid has solidified.

21. A prosthesis to be surgically positioned about the globe of an eye, comprising an elongated strip of biologically acceptable material having suturable ends and a length in the range of about 50-75 mm., and a pressure pad carried by the strip intermediate its length for bearing anteriorly against the eye wall obverse to the macula.

22. A method for applying anterior pressure upon the eye wall obverse to the macula, comprising
   providing a prosthesis comprising a longitudinal strip of biologically acceptable material bearing intermediate its length a pressure pad, and
   affixing said prosthesis to the eye wall with the pressure pad bearing anteriorly against the eye wall obverse to the macula.

23. The method of claim 22 wherein the prosthesis, as positioned against the wall of an eye, includes exteriorly operable tensioning means for adjusting tension of the strip, the method including the step of adjusting such tension.

24. The method of claim 23 wherein the tension-adjusting step is performed postoperatively.

* * * * *